(12) United States Patent
Ramachandran et al.

(10) Patent No.: US 8,440,874 B2
(45) Date of Patent: May 14, 2013

(54) OLEFIN ISOMERIZATION AND METATHESIS CATALYST

(75) Inventors: Bala Ramachandran, Easton, PA (US); Sukwon Choi, Clifton, NJ (US); Robert J. Gartside, Summit, NJ (US); Shane Kleindienst, Succasunna, NJ (US); Wolfgang Ruettinger, East Windsor, NJ (US); Saeed Alerasool, Princeton Junction, NJ (US)

(73) Assignees: Lummus Technology Inc., Bloomfield, NJ (US); BASF Corporation, Florham Park, NJ (US)

( * ) Notice: Subject to any disclaimer, the term of this patent is extended or adjusted under 35 U.S.C. 154(b) by 638 days.

(21) Appl. No.: 12/554,805

(22) Filed: Sep. 4, 2009

(65) Prior Publication Data

US 2010/0056839 A1    Mar. 4, 2010

Related U.S. Application Data

(60) Provisional application No. 61/094,296, filed on Sep. 4, 2008.

(51) Int. Cl.
*C07C 6/04* (2006.01)
(52) U.S. Cl.
USPC ........... 585/643; 585/646; 585/647; 585/664; 585/670
(58) Field of Classification Search ............. 585/310, 585/643, 646, 647, 664, 670
See application file for complete search history.

(56) References Cited

U.S. PATENT DOCUMENTS

| | | | |
|---|---|---|---|
| 2,930,803 A * | 3/1960 | Holmes et al. | 552/265 |
| 3,865,751 A * | 2/1975 | Banks et al. | 502/251 |
| 3,915,897 A | 10/1975 | Reusser et al. | |
| 4,542,249 A * | 9/1985 | Reusser | 585/329 |
| 4,559,320 A * | 12/1985 | Reusser | 502/251 |

(Continued)

FOREIGN PATENT DOCUMENTS

| GB | 1338429 | * 11/1973 |
|---|---|---|
| WO | WO 2006093058 A1 | * 9/2006 |

OTHER PUBLICATIONS

Gates, "Catalysis" in Kirk-Othmer Encyclopedia of Chemical Technology, John Wiley & Sons, published on-line Aug. 16, 2002.*

(Continued)

*Primary Examiner* — In Suk Bullock
*Assistant Examiner* — Bradley Etherton
(74) *Attorney, Agent, or Firm* — Osha • Liang LLP (57) ABSTRACT

A process for the production of propylene, the process including: contacting ethylene and a hydrocarbon stream comprising 1-butene and 2-butene with a bifunctional isomerization-metathesis catalyst to concurrently isomerizes 1-butene to 2-butene and to form a metathesis product comprising propylene; wherein the bifunctional isomerization-metathesis catalyst comprises: a catalyst compound may include at least one element selected from tungsten, tantalum, niobium, molybdenum, nickel, palladium, osmium, iridium, rhodium, vanadium, ruthenium, and rhenium for providing metathesis activity on a support comprising at least one element from Group IA, IIA, IIB, and IIIA of the Periodic Table of the Elements; wherein an exposed surface area of the support provides both isomerization activity for the isomerization of 1-butene to 2-butene; and reactive sites for the adsorption of catalyst compound poisons. In other embodiments, the catalyst compound may include at least one element selected from aluminum, gallium, iridium, iron, molybdenum, nickel, niobium, osmium, palladium, phosphorus, rhenium, rhodium, ruthenium, tantalum, titanium, tungsten, and vanadium.

14 Claims, 1 Drawing Sheet

U.S. PATENT DOCUMENTS

| | | | |
|---|---|---|---|
| 4,575,575 A | | 3/1986 | Drake et al. |
| 4,675,307 A | * | 6/1987 | Taniguchi et al. ............ 502/306 |
| 5,087,780 A | | 2/1992 | Arganbright |
| 5,177,291 A | * | 1/1993 | Knuuttila et al. ............. 585/646 |
| 5,898,091 A | | 4/1999 | Chodorge et al. |
| 6,075,173 A | | 6/2000 | Chodorge et al. |
| 6,130,181 A | | 10/2000 | Schwab et al. |
| 6,271,430 B2 | | 8/2001 | Schwab et al. |
| 6,307,117 B1 | | 10/2001 | Tsunoda et al. |
| 6,358,482 B1 | | 3/2002 | Chodorge et al. |
| 6,420,619 B1 | | 7/2002 | Gartside et al. |
| 6,580,009 B2 | | 6/2003 | Schwab et al. |
| 6,646,172 B1 | * | 11/2003 | Schwab et al. ................ 585/324 |
| 6,683,019 B2 | | 1/2004 | Gartside et al. |
| 6,727,396 B2 | | 4/2004 | Gartside |
| 6,743,958 B2 | | 6/2004 | Commereuc et al. |
| 6,777,582 B2 | | 8/2004 | Gartside et al. |
| 7,214,841 B2 | | 5/2007 | Gartside et al. |
| 7,223,895 B2 | | 5/2007 | Sumner |
| 2003/0028063 A1 | | 2/2003 | Gartside et al. |
| 2005/0080307 A1 | | 4/2005 | Voskoboynikov et al. |
| 2005/0250969 A1 | | 11/2005 | Bridges |
| 2006/0089517 A1 | | 4/2006 | Podrebarac et al. |
| 2008/0146856 A1 | | 6/2008 | Leyshon |
| 2010/0145126 A1 | * | 6/2010 | Takai et al. ................... 585/646 |

OTHER PUBLICATIONS

International Search Report and Written Opinion issued Mar. 30, 2010 in corresponding International Application No. PCT/US2009/056076 (10 pages).

First Examiner's Report issued May 8, 2012 in corresponding Canadian application No. 2,733,601 (3 pages).

Extended European search report issued Sep. 20, 2012 in corresponding European application No. 09812299.7(7 pages).

Office Action (w/translation) issued Oct. 22, 2012 in corresponding Korean application No. 10-2011-7007733 (12 pages).

Office Action (w/translation) issued Feb. 27, 2013 in corresponding Chinese application No. 200980134504.X (12 pages).

* cited by examiner

OLEFIN ISOMERIZATION AND METATHESIS CATALYST

CROSS-REFERENCE TO RELATED APPLICATION

This application, pursuant to 35 U.S.C. §119(e), claims priority to U.S. Provisional Application Ser. No. 61/094,296, filed Sep. 4, 2008, which is incorporated herein in its entirety.

BACKGROUND OF DISCLOSURE

1. Field of the Disclosure

Embodiments disclosed herein relate generally to the processing of a $C_3$ to $C_6$ hydrocarbon cut from a cracking process, such as steam or fluid catalytic cracking, primarily for conversion of $C_4$ olefins to propylene via metathesis.

2. Background

In typical olefin plants, such as illustrated in U.S. Pat. No. 7,223,895, there is a front-end demethanizer for the removal of methane and hydrogen followed by a deethanizer for the removal of ethane, ethylene and $C_2$ acetylene. The bottoms from this deethanizer tower consist of a mixture of compounds ranging in carbon number from $C_3$ to $C_6$. This mixture may be separated into different carbon numbers, typically by fractionation.

The $C_3$ cut, primarily propylene, is removed as product and is ultimately used for the production of polypropylene or for chemical synthesis such as propylene oxide, cumene, or acrylonitrile. The methyl acetylene and propadiene (MAPD) impurities must be removed either by fractionation or hydrogenation. Hydrogenation is preferred since some of these highly unsaturated $C_3$ compounds end up as propylene thereby increasing the yield.

The $C_4$ cut, consisting of $C_4$ acetylenes, butadiene, iso- and normal butenes, and iso- and normal butane can be processed in many ways. A typical steam cracker $C_4$ cut contains the following components in weight %:

TABLE 1

Typical $C_4$ cut components and weight percentages.

| | |
|---|---|
| $C_4$ Acetylenes | Trace |
| Butadiene | 33% |
| 1-butene | 15% |
| 2-butene | 9% |
| Isobutylene | 30% |
| Iso- and Normal Butanes | 13% |

The components in a refinery or FCC based $C_4$ cut are similar, with the exception that the percentage of paraffins are considerably greater.

Typically, the butadiene and $C_4$ acetylenes are removed first. This can be accomplished by either hydrogenation or extraction. The product from butadiene and $C_4$ acetylene removal is designated Raffinate I. If extraction is employed, the remaining 1-butene and 2-butene remain essentially in the same ratio as that of the initial feedstock. If hydrogenation is employed, the initial product from butadiene hydrogenation is 1-butene. Subsequently, hydroisomerization occurs within the same reaction system changing the 1-butene to 2-butene. The extent of this reaction depends upon catalyst and reaction conditions within the hydrogenation system. However, it is common practice to limit the extent of hydroisomerization in order to avoid "over hydrogenation" and the production of butanes from butenes. This would represent a loss of butene feedstock for downstream operations. The butenes remaining in the mixture consist of normal olefins (1-butene, 2-butene) and iso-olefins (isobutylene). The balance of the mixture consists of both iso- and normal-butanes from the original feed plus what was produced in the hydrogenation steps and any small quantity of unconverted or unrecovered butadiene.

A Raffinate I stream can be further processed in many ways. A Raffinate II stream is by definition a stream following isobutylene removal. Isobutylene can be removed in a number of ways. It can be removed via fractionation. In fractionation isobutane will be removed along with the isobutylene. In addition, some fraction of the 1-butene will be lost as well. The resultant Raffinate II will contain primarily normal olefins and paraffins and minimal isoolefins and isoparaffins. Isobutylene can also be removed via reaction. Reactions include: reaction with methanol to form MTBE, reaction with water to form tertiary butyl alcohol, or reaction with itself to form a $C_8$ gasoline component. In all reaction cases, the paraffins are not removed, and thus the mixture will contain both normal and iso-paraffins. The paraffin content and composition of the Raffinate II impacts downstream processing options.

The butenes have many uses. One such use is for the production of propylene via metathesis. Another is for the production of ethylene and hexene via metathesis. Conventional metathesis involves the reaction of normal butenes (both 1-butene and 2-butene) with ethylene (principally the reaction of 2-butene with ethylene to form propylene). These reactions occur in the presence of a group VIA or VIIA metal oxide catalyst, either supported or unsupported. The paraffin components of the reaction feed are essentially inert and do not react, and are typically removed from the process via a purge stream in the separation system that follows the metathesis reactor. Typical catalysts for metathesis are tungsten oxide supported on silica or rhenium oxide supported on alumina. Examples of catalysts suitable for the metathesis of olefins are described in U.S. Pat. Nos. 6,683,019 and 6,420,619, for example. Isobutylene (isobutene) may be removed from the feedstock prior to the metathesis reaction step. The reaction of isobutylene with ethylene is non-productive and reaction with itself and/or other $C_4$'s is limited in the presence of excess ethylene. Non-productive reactions essentially occupy catalyst sites but produce no product. If allowed to remain in the feed to the metathesis unit, the concentration of this non-reactive species would build up creating capacity limitations. The reaction of 1-butene with ethylene is also non-productive. However, it is common to employ a double bond isomerization catalyst within the metathesis reactor to shift 1-butene to 2-butene and allow for continued reaction. Typical double bond isomerization catalysts include basic metal oxides (Group IIA), either supported or unsupported. Magnesium oxide and calcium oxide are examples of such double bond isomerization catalysts that may be physically admixed with the metathesis catalyst. No equivalent co-catalyst exists for the skeletal isomerization of isobutylene to normal butene. In the case of a conventional metathesis system employing both a metathesis catalyst and a co-mixed double bond isomerization catalyst, the butadiene must be removed to a level of less than 500 ppm to avoid rapid fouling of the double bond isomerization catalyst. The metathesis catalyst itself can tolerate butadiene levels up to 10,000 ppm.

In some cases, an isobutylene removal step is employed prior to metathesis. Options include reacting it with methanol to produce methyl tertiary butyl ether (MTBE) or separating the isobutylene from the butenes by fractionation. U.S. Pat. No. 6,358,482 discloses the removal of isobutylene from the $C_4$ mixture prior to metathesis. This scheme is further reflected in U.S. Pat. Nos. 6,075,173 and 5,898,091. U.S. Pat. No. 6,580,009 discloses a process for the production of propylene and hexene from a limited ethylene fraction. For molar ratios of ethylene to butenes (expressed as n-butenes) from 0.05 to 0.60, the inventors utilize a Raffinate II stream as the $C_4$ feedstock.

The typical metathesis process takes the Raffinate I feedstock and removes the majority of the isobutylene via fractionation, as described above to form a Raffinate II. In this step, the isobutene is removed as well plus some quantities of normal butenes, dependent upon the fractionation conditions. The Raffinate II is then admixed with ethylene, passed through guard beds to remove poisons, vaporized and preheated and fed to the metathesis reactors. The operating conditions are typically 300° C. and 20 to 30 bar pressure. The reactor effluent following heat recovery is then separated in a fractionation system. First the ethylene is recovered overhead in a first tower and recycled to the reactor system. The tower bottoms are then sent to a second tower where the propylene is recovered overhead. A side draw is taken containing the majority of the unconverted $C_4$ components and recycled to the reactor. The tower bottoms containing the $C_5$ and heavier products plus $C_4$ olefins and paraffins are sent to purge. The purge rate is typically fixed to contain sufficient $C_4$ paraffins to avoid their buildup in the reactor recycle stream. In some cases, a third tower is employed on the tower bottoms stream to separate the $C_4$ components overhead and the $C_5$ and heavier components as a bottoms stream.

U.S. Pat. No. 6,271,430 discloses a two-step process for the production of propylene. The first step consists of reacting 1-butene and 2-butene in a raffinate II stream in an auto-metathesis reaction to form propylene and 2-pentene. The products are then separated in the second step. The third step reacts specifically the 2-pentene with ethylene to form propylene and 1-butene. This process utilizes the isobutylene free raffinate II stream. The pentenes recycled and reacted with ethylene are normal pentenes (2-pentene).

Isobutylene removal from the $C_4$ stream can also be accomplished by employing a combined catalytic distillation hydroisomerization deisobutyleneizer system to both remove the isobutylene and recover n-butenes at high efficiency by isomerizing the 1-butene to 2-butene with known isomerization catalysts and thus increasing the volatility difference. This technology combines conventional fractionation for isobutylene removal with hydroisomerization within a catalytic distillation tower. In U.S. Pat. No. 5,087,780 to Arganbright, 2-butene is hydroisomerized to 1-butene as the fractionation occurs. This allows greater than equilibrium amounts of 1-butene to be formed as the mixture is separated. Similarly, 1-butene can be hydroisomerized to 2-butene in a catalytic distillation tower. In separating a $C_4$ stream containing isobutylene, 1-butene, and 2-butene (plus paraffins), it is difficult to separate isobutylene from 1-butene since their boiling points are very close. By employing simultaneous hydroisomerization of the 1-butene to 2-butene with fractionation of isobutylene, isobutylene can be separated from the normal butenes at high efficiency.

The metathesis reaction described above is equimolar, i.e., one mole of ethylene reacts with 1 mole of 2-butene to produce 2 moles of propylene. However, commercially, in many cases, the quantity of ethylene available is limited with respect to the quantity of butenes available. In addition, the ethylene is an expensive feedstock and it is desired to limit the quantities of ethylene used. As the ratio of ethylene to butenes is decreased, there is a greater tendency for the butenes to react with themselves which reduces the overall selectivity to propylene.

The metathesis catalysts and the double bond isomerization catalysts are quite sensitive to poisons. Poisons include water, $CO_2$, oxygenates (such as MTBE), sulfur compounds, nitrogen compounds, and heavy metals. It is common practice to employ guard beds upstream of the metathesis reaction system to insure the removal of these poisons. It does not matter if these guard beds are directly before the metathesis reaction system or further upstream as long as the poisons are removed and no new poisons are subsequently introduced.

Metathesis reactions are very sensitive to the location of the olefin double bond and the stereo-structure of the individual molecules. During the reaction, the double bond on each pair of olefins adsorb on the surface and exchange double bond positions with the carbon groups on either sides of the double bonds. Metathesis reactions can be classified as productive, half productive or non-productive. As described above, non-productive reactions result in essentially no reaction taking place. When the double bonds shift with metathesis reaction, the new molecules are the same as the originally adsorbed molecules thus no productive reaction occurs. This is typical for reactions between symmetric olefins or reactions between ethylene and alpha olefins. If fully productive reactions occur, new products are generated no matter which orientation the molecules occupy the sites. The reaction between ethylene and 2-butene to form two propylene molecules is a fully productive reaction. Half productive reactions are sterically inhibited. If the pair of olefins adsorb in one orientation (typically the cis position with respect to the attached R groups), when the double bonds shift, new products are formed. Alternately if they adsorb in a different steric configuration (the trans position), when the bonds shift, the identical olefins are formed and thus no new products are formed. The various metathesis reactions proceed at different rates (a fully productive reaction is usually faster than a half productive reaction). Table 2 summarizes the reactions between ethylene and various butenes and the reactions between the butenes themselves.

The reactions listed in Table 2 represent the base reaction with ethylene (reaction 1, 4 and 5) as well as the reactions between the various $C_4$ olefins. It is especially important to make a distinction between the selectivity to propylene from total $C_4$ olefins (including isobutylene) and the selectivity to propylene from the normal $C_4$ olefins involved in the reaction. The reaction of isobutylene with 2-butene (reaction 6) produces propylene and a branched $C_5$ molecule. For this reaction, propylene is produced at 50 molar % selectivity from total $C_4$'s (similar to reaction 2) but at a 100 molar % selectivity from the normal $C_4$ (2-butene). For the purposes of definitions, conventional metathesis is defined as the reaction of the $C_4$ olefin stream with ethylene. However, the $C_4$ stream can also react in the absence of ethylene as a feedstock. This reaction is called auto or self metathesis. In this case, reactions 2, 3, 6, and 7 are the only possible reactions and will occur at rates dependent upon the feedstock composition.

TABLE 2

| No. | Reaction | Type | Rate | Molar % Selectivity ($C_3H_6$ from total $C_4$s) | Molar % Selectivity ($C_3H_6$ from n-$C_4$s) |
|---|---|---|---|---|---|
| 1 | 2-butene + ethylene → 2 propylene (Conventional Metathesis) | Fully Productive | Fast | 100 | 100 |

TABLE 2-continued

| No. | Reaction | Type | Rate | Molar % Selectivity ($C_3H_6$ from total $C_4$s) | Molar % Selectivity ($C_3H_6$ from n-$C_4$s) |
|---|---|---|---|---|---|
| 2 | 1-butene + 2-butene → Propylene + 2-pentene | Fully Productive | Fast | 50 | 50 |
| 3 | 1-butene + 1-butene → Ethylene + 3-hexene | Half Productive | Slow | 0 | 0 |
| 4 | Isobutylene + Ethylene → No reaction | Non-productive | No Reaction | — | — |
| 5 | 1-butene + ethylene → No reaction | Non-productive | No Reaction | | |
| 6 | Isobutylene + 2-butene → Propylene + 2-methyl 2-butene | Fully Productive | Fast | 50 | 100 |
| 7 | Isobutylene + 1-butene → ethylene + 2-methyl 2 pentene | Half productive | Slow | 0 | 0 |

In conventional metathesis, the focus is to maximize reaction 1 to produce propylene. This will maximize the selectivity to propylene. As such, excess ethylene is used to reduce the extent of the reactions of butenes with themselves (reactions 2, 3, 6, and 7). The theoretical ratio is 1/1 molar or 0.5 weight ratio of ethylene to n-butenes but it is common in conventional metathesis to employ significantly greater ratios, typically, 1.3 or larger molar ratio to minimize reactions 2, 3, 6 and 7. Under conditions of excess ethylene, and due to the fact that both isobutylene and 1-butene do not react with ethylene (see reactions 4 and 5), two process sequences are employed. First, the isobutylene is removed prior to metathesis. If isobutylene is not removed, it will build up as the n-butenes are recycled to achieve high yield. Second, 1-butene is isomerized to 2-butene by including a double bond isomerization catalyst such as magnesium oxide admixed with the metathesis catalyst. Note that this catalyst will not cause skeletal isomerization (isobutylene to normal butylenes) but only shift the double bond from the 1 position to the 2 position for the normal butenes. Thus by operating with excess ethylene, eliminating isobutylene from the metathesis feed prior to reaction, and employing a double bond isomerization catalyst, reaction 1 is maximized. Note, however, that by removing the isobutylene, potential production of propylene or other products is lost.

When there is limited or no fresh ethylene (or excess butylenes for the ethylene available), there are currently two options available for propylene production. In these cases, the first option will first remove the isobutylene and then process the normal butenes with whatever ethylene is available. The entire n-butenes-only mixture is subjected to metathesis with the available ethylene. Ultimately, if there is no fresh ethylene available, the $C_4$'s react with themselves (auto metathesis). Under low ethylene conditions, reactions 2, 3, 6 and 7 will occur, all leading to a lower propylene selectivity (50% or lower versus 100% for reaction 1). The lower selectivity results in lower propylene production. Note that reactions 6 and 7 will be minimized as a result of the removal of isobutylene (to low levels but not necessarily zero). Alternately, the molar flows of ethylene and butenes can be matched by limiting the flow of butenes to produce conditions where there is a high selectivity of the normal butenes to propylene via reaction 1. By limiting the flow of n-butenes to match ethylene, the production of propylene is limited by the reduced butenes flow.

Pentenes and some hexenes are formed to some extent in the conventional metathesis case with low ethylene via reactions 2 and 3. The volume of these components will depend upon the ethylene/n-butenes ratio with a lower ratio producing more $C_5$ and $C_6$ components. In the conventional prior art case where isobutylene is removed before any metathesis, these $C_5$ and $C_6$ olefins are normal olefins since no skeletal isomerization occurs. It is possible to recycle these olefins back to the metathesis step where, for example, the reaction with ethylene and 2-pentene will occur yielding propylene and 1-butene. The 1-butene is recovered and recycled. Note however, with limited ethylene, reaction 1 can occur only to the limit of the ethylene availability. Ultimately these non-selective byproducts, pentenes and hexenes, must be purged from the system.

U.S. Pat. No. 6,777,582 discloses a process for the auto-metathesis of olefins to produce propylene and hexene. Therein, auto-metathesis of a mixed normal butenes feed in the presence of a metathesis catalyst operates without any ethylene in the feed mix to the metathesis reactor. Some fraction of the 2-butene feed may be isomerized to 1-butene and the 1-butene formed plus the 1-butene in the feed react rapidly with the 2-butene to form propylene and 2-pentene. The feed to the reactor also includes the recycle of the 2-pentene formed in the reactor with unreacted butenes to simultaneously form additional propylene and hexene. The 3-hexene formed in the reaction may be isomerized to 1-hexene.

In U.S. Pat. No. 6,727,396, ethylene and hexene-1 are produced from butene-1 by metathesis of butene-1 and isomerization of the hexene-3 produced therein to hexene-1. The initial starting material is a mixed butene stream wherein butene-1 is isomerized to butene-2 with isobutylene being separated therefrom, followed by isomerization of butene-2 to butene-1, with the butene-1 being the feed to the metathesis.

In U.S. Pat. No. 7,214,841, the $C_4$ cut from a hydrocarbon cracking process is first subjected to auto-metathesis prior to any isobutylene removal and without any ethylene addition, favoring the reactions which produce propylene and pentenes. The ethylene and propylene produced are then removed leaving a stream of the C.sub.4's and heavier components. The C.sub.5 and heavier components are then removed leaving a mixture of 1-butene, 2-butene, isobutylene, and iso- and normal butanes. The isobutylene is next removed preferably by a catalytic distillation hydroisomerization de-isobutyleneizer. The isobutylene-free $C_4$ stream is then mixed with the product ethylene removed from the auto-metathesis product together with any fresh external ethylene needed and subjected to conventional metathesis producing additional propylene.

Another use of the $C_4$ olefin stream is as a feedstock to an olefin cracking process, where the olefins are reacted with themselves over a zeolitic catalyst to produce a mixture comprising ethylene, propylene, and aromatics (such as benzene). Similar to the metathesis process, the paraffins are inert in this cracking process and must be removed from the process via a purge stream. U.S. Pat. No. 6,307,117 and U.S. Patent Application Publication No. 20050080307 both describe such a process. A mixture of typically $C_4$ to $C_6$ olefins as well as paraffins is vaporized and fed to a reactor filled with a crystalline zeolitic catalyst and operating at a temperature between 450 and 600° C. and a pressure between 10 and 70 psia. The reactor effluent is first sent to a compression step. The cracking reactor system operates at relatively low pressure to avoid fouling of the catalyst in the cracking reactor. In order to reduce the energy costs due to refrigeration in the subsequent separation system, the pressure is typically increased to pressures on the order of 12 to 25 barg. This allows the subsequent fractionating towers to utilize cooling water instead of refrigeration in the overhead condensation step. The compression effluent is then sent to a separation system where the ethylene and propylene are recovered along with an aromatics stream. The ethylene and propylene is recovered overhead in a first tower. Unlike metathesis, these products contain sufficient quantities of ethane and propane that additional purification of this stream is necessary. This can be accomplished by additional fractionation or by utilizing the recovery system of an adjacent facility such as an olefins plant. The tower bottoms contains $C_4$, $C_5$ and $C_{6+}$ paraffins and aromatics. This is sent to a second tower. The overhead is a $C_4/C_5$ stream and the highly aromatic $C_{6+}$ stream is the bottoms product. The unconverted $C_4$ and $C_5$ products are typically recycled. The cracking process can handle both iso and normal olefins with equivalent efficiency. There is no need to remove isobutylene for example from the feed to maximize propylene production.

The isomerization and metathesis of olefins in the above-described processes currently utilizes two catalysts. For example, $WO_3/SiO_2$ catalyst may perform the metathesis reaction and MgO catalysts may perform the olefin isomerization reaction. The MgO catalyst also serves a reactive guard bed, which prevents the adsorption of poisons onto the $WO_3/SiO_2$ (metathesis) catalyst, and, therefore, prolongs its cycle length.

The two-catalyst system typically consists of a physical mixture of two catalysts. One is a tabletted MgO and the other is a silica supported $WO_3$ in the form of granules. The MgO catalyst is present to act both as a reactive guard bed and to provide isomerization of 1-butene to 2-butene for the reaction of 2-butene with ethylene to ultimately form two propylene molecules. These catalysts, when loaded as a (MgO: $WO/SiO_2$) bed with a part upper MgO bed, or an overall (MgO: $WO/SiO_2$) mixed bed, present several issues. For example, the MgO is subject to significant sintering and loss of surface area over catalyst regenerations; the loss of surface area results in loss of MgO activity for both isomerization and as an adsorbent of poisons. As another example, the mixed co-catalyst system may be subject to uneven mixing, bed non-uniformity, flow channeling, and uneven temperature distribution in the bed, which also further affects catalyst performance. Additionally, the reactive effectiveness of a physical mixture on a kinetic basis is lower than a single catalyst where the functionality is in close proximity.

As described above, there is considerable interest in the processing of $C_4$, $C_5$, and heavier olefin streams to produce lighter olefins, such as propylene. Accordingly, there exists a significant need for catalysts and processes that may result in the efficient isomerization and metathesis of linear butenes for the production of high purity propylene from such olefin-containing streams at low cost and low energy.

SUMMARY OF THE DISCLOSURE

In one aspect, embodiments disclosed herein relate to a process for the production of propylene, the process including: contacting ethylene and a hydrocarbon stream comprising 1-butene and 2-butene with a bifunctional isomerization-metathesis catalyst to concurrently isomerizes 1-butene to 2-butene and to form a metathesis product comprising propylene; wherein the bifunctional isomerization-metathesis catalyst comprises: a catalyst compound comprising at least one element selected from tungsten, tantalum, niobium, molybdenum, nickel, palladium, osmium, iridium, rhodium, vanadium, ruthenium, and rhenium for providing metathesis activity on a support comprising at least one element from Group IA, IIA, IIB, and IIIA of the Periodic Table of the Elements; wherein an exposed surface area of the support provides both isomerization activity for the isomerization of 1-butene to 2-butene; and reactive sites for the adsorption of catalyst compound poisons. Alternatively, the material having metathesis activity and the material having isomerization and poison adsorption activity can be co-mingled on a microscopic scale and then tabletted or extruded in the presence of a binder to form the bifunctional catalyst.

In another aspect, embodiments disclosed herein relate to a bifunctional isomerization-metathesis catalyst for the concurrent isomerization and metatheses of a mixed butene feed, including: a catalyst compound comprising at least one element selected from tungsten, tantalum, niobium, molybdenum, nickel, palladium, osmium, iridium, rhodium, vanadium, ruthenium, and rhenium for providing metathesis activity on a support comprising at least one element from Group IA, IIA, IIB, and IIIA of the Periodic Table of the Elements; wherein an exposed surface area of the support provides both isomerization activity for the isomerization of 1-butene to 2-butene; and reactive sites for the adsorption of catalyst compound poisons. Alternatively, the material having metathesis activity and the material having isomerization and poison adsorption activity can be co-mingled on a microscopic scale and then tabletted or extruded in the presence of a binder to form the bifunctional catalyst.

In another aspect, embodiments disclosed herein relate to a process of preparing a bifunctional isomerization-metathesis catalyst for the concurrent isomerization and metathesis of a mixed butene feed, including: calcining a support comprising at least one element from Group IA, IIA, IIB, and IIIA of the Periodic Table of the Elements; impregnating the calcined support with a catalyst compound comprising at least one element selected from tungsten, tantalum, niobium, molybdenum, nickel, palladium, osmium, iridium, rhodium, vanadium, ruthenium, and rhenium; wherein the catalyst compound element provides metathesis activity; and wherein an exposed surface area of the support provides both isomerization activity for the isomerization of 1-butene to 2-butene; and reactive sites for the adsorption of catalyst compound poisons. Alternatively, particles of material having metathesis activity and material having isomerization and poison adsorption activity are co-mingled on a microscopic scale and either tabletted or extruded in the presence of a binder to form the bifunctional catalyst.

In another aspect, embodiments disclosed herein relate to a process for the production of propylene, the process including: contacting ethylene and a hydrocarbon stream comprising 1-butene and 2-butene with a bifunctional isomerization-metathesis catalyst to concurrently isomerizes 1-butene to 2-butene and to form a metathesis product comprising propylene; wherein the bifunctional isomerization-metathesis catalyst comprises: a catalyst compound comprising at least one element selected from aluminum, gallium, iridium, iron, molybdenum, nickel, niobium, osmium, palladium, phosphorus, rhenium, rhodium, ruthenium, tantalum, titanium, tungsten, and vanadium for providing metathesis activity: co-mingled on a microscopic scale with a catalyst comprising at least one element from Group IA, IIA, IIB, and IIIA of the Periodic Table of the Elements; or on a support comprising at least one element from Group IA, IIA, IIB, and IIIA of the Periodic Table of the Elements; wherein the co-mingled catalyst particles or an exposed surface area of the support provides both isomerization activity for the isomerization of 1-butene to 2-butene; and reactive sites for the adsorption of catalyst poisons in the feed.

In another aspect, embodiments disclosed herein relate to a bifunctional isomerization-metathesis catalyst for the concurrent isomerization and metatheses of a mixed butene feed, including: a catalyst compound comprising at least one element selected from aluminum, gallium, iridium, iron, molybdenum, nickel, niobium, osmium, palladium, phosphorus, rhenium, rhodium, ruthenium, tantalum, titanium, tungsten, and vanadium for providing metathesis activity: co-mingled on a microscopic scale with a catalyst comprising at least one element from Group IA, IIA, IIB, and IIIA of the Periodic Table of the Elements; or on a support comprising at least one element from Group IA, IIA, IIB, and IIIA of the Periodic Table of the Elements; wherein an exposed surface area of the support provides both isomerization activity for the isomerization of 1-butene to 2-butene; and reactive sites for the adsorption of catalyst poisons in the feed.

In another aspect, embodiments disclosed herein relate to a process of preparing a bifunctional isomerization-metathesis catalyst for the concurrent isomerization and metathesis of a mixed butene feed, including: impregnating a support comprising at least one element from Group IA, IIA, IIB, and IIIA of the Periodic Table of the Elements with a catalyst compound comprising at least one element selected from aluminum, gallium, iridium, iron, molybdenum, nickel, niobium, osmium, palladium, phosphorus, rhenium, rhodium, ruthenium, tantalum, titanium, tungsten, and vanadium; wherein the catalyst compound element provides metathesis activity; and wherein an exposed surface area of the support provides both isomerization activity for the isomerization of 1-butene to 2-butene; and reactive sites for the adsorption of catalyst compound poisons.

In another aspect, embodiments disclosed herein relate to a process of preparing a bifunctional isomerization-metathesis catalyst for the concurrent isomerization and metathesis of a mixed butene feed, including: co-mingling a first compound comprising at least one element from Group IA, IIA, IIB, and IIIA of the Periodic Table of the Elements with a catalyst compound comprising at least one element selected from aluminum, gallium, iridium, iron, molybdenum, nickel, niobium, osmium, palladium, phosphorus, rhenium, rhodium, ruthenium, tantalum, titanium, tungsten, and vanadium to form a mixture; forming the mixture into a catalyst particle; wherein the catalyst compound element provides metathesis activity; and wherein the first compound element provides both isomerization activity for the isomerization of 1-butene to 2-butene; and reactive sites for the adsorption of catalyst poisons in the feed.

Other aspects and advantages will be apparent from the following description and the appended claims.

DETAILED DESCRIPTION

In one aspect, embodiments herein relate to the processing of a $C_4$ to $C_6$ hydrocarbons to form lighter olefins, such as ethylene and propylene. In another aspect, embodiments disclosed herein relate to the concurrent isomerization of 1-olefins, such as 1-butene, to 2-olefins, such as 2-butene, and the metathesis of the 2-olefins to form propylene and ethylene. In other aspects, embodiments disclosed herein relate to a bifunctional catalyst for the concurrent isomerization and metathesis, and a method of preparing the bifunctional catalyst.

In a more specific aspect, embodiments disclosed herein relate to a process for the production of propylene, including contacting ethylene and a hydrocarbon stream including 1-butene with a bifunctional isomerization-metathesis catalyst to concurrently isomerizes 1-butene to 2-butene and to form a metathesis product including propylene.

In some embodiments, the hydrocarbon stream including 1-butene may be supplied as a mixed $C_4$ stream. The mixed $C_4$ feed to processes disclosed herein may include $C_3$ to $C_{6+}$ hydrocarbons, including $C_4$, $C_4$ to $C_5$, and $C_4$ to $C_6$ cracker effluents, such as from a steam cracker or a fluid catalytic cracking (FCC) unit. Other refinery hydrocarbon streams containing a mixture of $C_4$ olefins may also be used. When $C_3$, $C_5$ and/or $C_6$ components are present in the feed, the stream may be pre-fractionated to result in a primary $C_4$ cut, a $C_4$ to $C_5$ cut, or a $C_4$ to $C_6$ cut.

$C_4$ components contained in the feed stream may include n-butane, isobutane, isobutene, 1-butene, 2-butene, and butadiene. In some embodiments, the mixed $C_4$ feed is pretreated to provide a 1-butene feed for the metathesis reaction. For example, when butadiene is present in the $C_4$ feed, the butadiene may be removed via hydrogenation or extraction. In other embodiments, the mixed butenes feed following or in conjunction with butadiene hydrogenation may be subjected to hydroisomerization conditions to convert 1-butene to 2-butene, with isobutylene being separated from a 2-butene stream by fractionation. The 2-butene stream may then be isomerized back to 1-butene in a subsequent step for use as feed to the metathesis portion of the processes disclosed herein.

The 1-butene may then be contacted with a bifunctional isomerization-metathesis catalyst to concurrently isomerize at least a portion of the 1-butene to 2-butene, and to metathesize at least a portion of the 2-butene to form one or more metathesis products including ethylene, propylene, and $C_5$ to $C_6$ metathesis products. In some embodiments, the 2-butene may be subject to conventional metathesis, where ethylene is co-fed with the 2-butene to the metathesis reactor.

The metathesis reactor may operate at a pressure between 2 and 40 atmospheres in some embodiments, and between 5 and 15 atmospheres in other embodiments. The metathesis reactor may be operated such that the reaction temperature is within the range from about 50° C. to about 600° C.; within the range from about 200° C. to about 450° C. in other embodiments; and from about 250° C. to about 400° C. in yet other embodiments. The metathesis reaction may be performed at a weight hourly space velocity (WHSV) in the range from about 3 to about 200 in some embodiments, and from about 6 to about 40 in other embodiments.

The reaction may be carried out by contacting the olefin(s) with the bifunctional isomerization-metathesis catalyst in the liquid phase or the gas phase depending on structure and molecular weight of the olefin(s). If the reaction is carried out in the liquid phase, solvents or diluents for the reaction can be used. Aliphatic saturated hydrocarbons, e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, and/or substantially inert gases, such as nitrogen and argon, may be present. For high product yield, the reaction may be conducted in the absence of significant amounts of deactivating materials such as water and oxygen.

The contact time needed to obtain a desirable yield of metathesis reaction products depends upon several factors such as the activity of the catalyst, temperature, pressure, and the structure of the olefin(s) to be metathesized. Length of time during which the olefin(s) are contacted with catalyst can conveniently vary between 0.1 seconds and 4 hours, preferably from about 0.5 sec to about 0.5 hrs. The metathesis reaction may be conducted batch-wise or continuously with fixed catalyst beds, slurried catalyst, fluidized beds, or by using any other conventional contacting techniques.

In some embodiments, the concurrent isomerization and metathesis reaction may be conducted in the presence of hydrogen. In the presence of hydrogen, the bifunctional isomerization-metathesis catalyst may reduce 1,3-butadiene production during the reaction by 95% or more as compared to commercial mixed bed catalyst system. 1,3-butadiene may cause catalyst coking under reaction conditions, and with the lower production of 1,3-butadiene when hydrogen is used, catalyst fouling by 1,3-butadiene is drastically reduced. The use of hydrogen with the bifunctional isomerization-metathesis catalyst thus increases cycle length over mixed bed catalyst systems.

In some embodiments, the bifunctional isomerization-metathesis catalyst may include a catalyst compound comprising at least one element selected from aluminum, gallium, iridium, iron, molybdenum, nickel, niobium, osmium, palladium, phosphorus, rhenium, rhodium, ruthenium, tantalum, titanium, tungsten, and vanadium for providing metathesis activity on a support comprising at least one element from Group IA, IIA, IIB, and IIIA of the Periodic Table of the Elements. In other embodiments, the bifunctional isomerization-metathesis catalyst may include a catalyst compound comprising at least one element selected from tungsten, tantalum, niobium, molybdenum, nickel, palladium, osmium, iridium, rhodium, vanadium, ruthenium, and rhenium for providing metathesis activity on a support comprising at least one element from Group IA, IIA, IIB, and IIIA of the Periodic Table of the Elements. The support material is selected such that an exposed surface area of the support provides both a) isomerization activity for the isomerization of 1-butene to 2-butene and b) reactive sites for the adsorption of catalyst compound poisons.

In some embodiments, the support may include an oxide, sulfide, nitride, or hydride of the at least one element from Group IA, IIA, IIB, and IIIA of the Periodic Table of the Elements. For example, the support may include a basic metal oxide suitable for the isomerization of 1-butene to 2-butene, such as magnesium oxide, calcium oxide, barium oxide, lithium oxide, sodium oxide, and potassium oxide, and mixtures thereof.

In some embodiments, the support may include a magnesia-alumina hydrotalcite. Hydrotalcite compounds suitable to perform isomerization and poison adsorption may include, for example, the hydrotalcite compounds disclosed in U.S. Pat. No. 4,675,307, which is incorporated herein by reference.

The bifunctional isomerization-metathesis catalyst for the concurrent isomerization and metathesis of a mixed butene feed may be prepared by first calcining a support comprising at least one element from Group IA, IIA, IIB, and IIIA of the Periodic Table of the Elements. The catalyst may then be loaded onto the calcined support, where the catalyst compound comprises at least one element selected from aluminum, gallium, iridium, iron, molybdenum, nickel, niobium, osmium, palladium, phosphorus, rhenium, rhodium, ruthenium, tantalum, titanium, tungsten, and vanadium in some embodiments, and selected from tungsten, tantalum, niobium, molybdenum, nickel, palladium, osmium, iridium, rhodium, vanadium, ruthenium, and rhenium in other embodiments. The catalyst or a catalyst precursor may be loaded onto the support via any known method, including an impregnation method, an incipient wetness method, or an ion-exchange method.

For example, a bifunctional isomerization-metathesis catalyst may be prepared by calcining hydrotalcite at a temperature of at least 350° C. The calcined hydrotalcite may then be impregnated with a metathesis catalyst precursor, such as ammonium metatungstate. In some embodiments, the hydrotalcite may be calcined, formed into a shape suitable for a commercial reactor, and then impregnated with a catalyst or catalyst precursor. Shapes suitable for a commercial reactor may include powders, pellets, extrudates, and the like.

In some embodiments, the impregnated catalyst may be contacted with an alkali metal promoter. For example, the alkali metal promoter may include at least one of sodium, potassium, lithium, cesium, and a rare earth element. The alkali metal promoter may reduce the acidity of the catalyst and/or exposed surface areas of the support. In other embodiments, the metathesis catalyst and the isomerization catalyst are co-mingled on a microscopic scale and formed (e.g., tabletted or extruded in the presence of a binder) into a catalyst particle. The mixing is achieved using a blender or other powder mixing devices. In some embodiments, the blended materials are mixed with water, acid or base and a binder like silica, clay, titania, zirconia, alumina and the like to form an extrudable mixture. This mixture can be extruded and/or formed into any suitable shape including cylinders, cubes, stars, tri-lobes, quadra-lobes, pellets, pills, spheres, or shapes containing hollow cores of varying diameters by suitable mechanical means.

For some of the above-described bifunctional isomerization-metathesis catalysts, it has been found that calcining must be performed prior to catalyst impregnation. For example, impregnating a hydrotalcite with an ammonium metatungstate solution and then calcining the powder will result in an inactive catalyst. Hydrotalcite has intermittent layers of hydroxides and carbonates that release upon calcination at temperatures above 350 C. If, however, the hydrotalcite is calcined first, the resultant MgO/Al$_2$O$_3$ solution will have high surface area and be very stable. Impregnating this material with the same ammonium metatungstate solution results in a catalyst that has a high metathesis activity. Additionally, the hydrotalcite material, once calcined, retains a high surface area/gram over a number of regenerations. Thus, the MgO portion surface area does not decrease, allowing for high isomerization activity and poison adsorption (guard bed activity) to be maintained.

Prior to use, bifunctional isomerization-metathesis catalysts formed as described above may be activated, such as by oxidation of the metathesis catalyst precursor or by other techniques known to those skilled in the art.

Bifunctional isomerization-metathesis catalyst disclosed herein may include up to about 30 weight percent of a metal oxide having metathesis activity. In other embodiments, the bifunctional isomerization-metathesis catalyst may contain between 1 and 25 weight percent of a metal oxide having metathesis activity; between 6 and 7 weight percent of a metal oxide having metathesis activity, such as tungsten oxide, in other embodiments.

For example, a bifunctional catalyst according to embodiments disclosed herein may include a 70% MgO, 30% alumina support carrying 6-7% tungsten oxide ($WO_3$). The $WO_3$ loading is equivalent to that on commercially available monofunctional metathesis catalysts. However, due to the volume loading in a metathesis reactor when mixed with an isomerization catalyst, the bifunctional catalysts disclosed herein allow for a similar amount of isomerization/guard bed catalyst to be added to a reactor with a substantial increase in the quantity of metathesis catalyst. For example, up to five times higher tungsten weight per unit volume can be achieved with the bifunctional catalysts compared to commercial mixed bed catalyst system. This higher tungsten loading may result in longer catalyst cycle life.

Further, a single bifunctional catalyst eliminates the blending process of two different catalysts of dissimilar morphology during the manufacturing process. Blending may result in fines generation during mixing, transport, and loading of the separate catalysts in reactor. Fines generation in a reactor results in increased pressure drop. All of this is eliminated by the use of the single catalyst.

As described above, ethylene and a hydrocarbon stream including 1-butene may be contacted, in the presence or absence of hydrogen, with a bifunctional isomerization-metathesis catalyst to concurrently isomerizes 1-butene to 2-butene and to form a metathesis product including propylene. The effluent from the isomerization-metathesis reactor may also include unreacted components (ethylene, butenes, hydrogen, etc.) and other metathesis byproducts.

The effluent from the metathesis reactor may be sent to a separation system to separate the metathesis effluent into carbon number groups by technology well known in the art. For example, the products of the separation system may include an ethylene stream, a propylene stream, a $C_4$ stream, and a $C_{5+}$ stream. The propylene stream may be recovered as a product stream, which may also undergo further purification steps to obtain a high purity propylene product. The $C_4$ stream may be recycled back to the metathesis reactor or a pretreatment stage, such as isomerization or fractionation. The ethylene stream may also be recovered as a product stream or may be recycled back to the metathesis reactor for use as an ethylene feedstock for the conventional metathesis reaction.

In some embodiments, an olefin feed to a conventional metathesis reactor may include essentially pure normal butenes. This can be any mixture of 1-butene and 2-butene and may also contain $C_4$ paraffins as a feed diluent. In some embodiments, the isobutene content, based on a combined amount of olefins in the feed mixture; may be less than 10%; less than 5% in other embodiments; less than 2% in other embodiments; and less than 1% in yet other embodiments.

In other embodiments, isobutene feed specifications may be relaxed, thus allowing some flexibility for ethylene feed to the metathesis reactor. For example, feeding some isobutene, such as up to an isobutene concentration in the mixed $C_4$ feed of about 15%, to the metathesis reactor may allow the reduction in the overall energy costs as the fractionation requirements are reduced. This flexibility may advantageously allow for lower capital costs, due to the relaxed separation requirements, as well as the potential for the metathesis process according to embodiments disclosed herein to operate with a low ethylene consumption. In some embodiments, a ratio of ethylene to butenes in a conventional metathesis reactor feed may range from about 0.1 to about 2.5. In other embodiments, a ratio of ethylene to butenes in a conventional metathesis reactor feed may range from about 0.8 to about 2.0; and from about 1.5 to about 2.0 in yet other embodiments.

Figure 1:
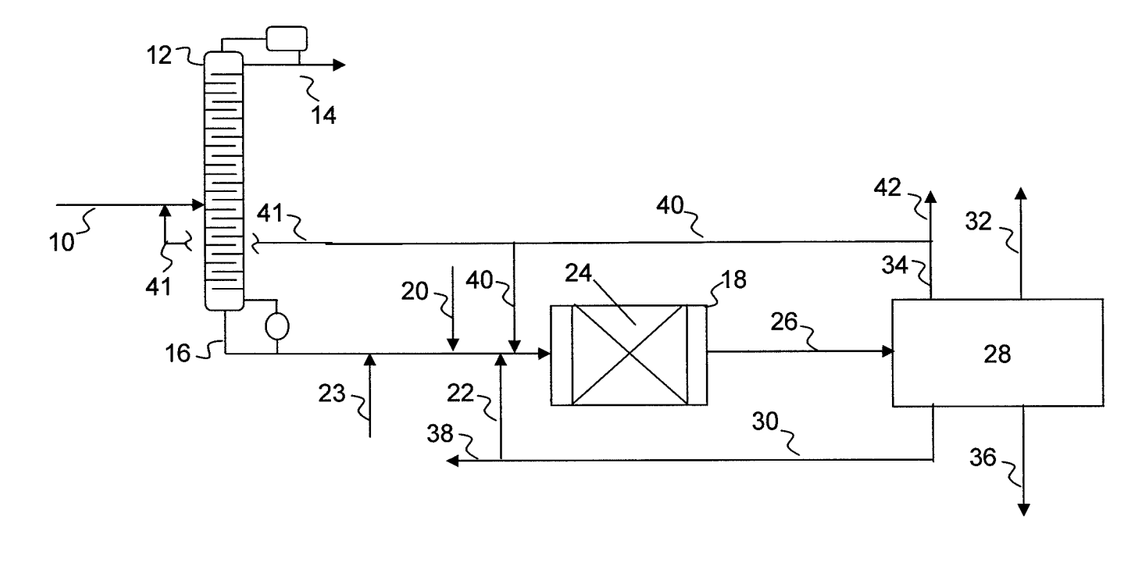
FIG. 1 is a simplified process flow diagram of a process for producing propylene according to embodiments disclosed herein.

Referring now to FIG. 1, a simplified process flow diagram of a process for producing propylene according to embodiments disclosed herein is illustrated. A mixed $C_4$ stream containing n-butenes, isobutylene, and paraffins may be fed via flow line 10 to a fractionator 12, where the $C_4$s may be fractionated into at least two fractions, including a light $C_4$ fraction, including isobutylene, and a heavy $C_4$ fraction, including n-butenes. The light $C_4$ fraction may be recovered from fractionator 12 as an overheads fraction via flow line 14. Fractionator 12 may be either a conventional fractionation tower or may be a catalytic distillation fractionation tower wherein a catalyst is utilized to isomerizes 1-butene to 2-butene and hydrogenate butadiene to 1- or 2-butene while simultaneously separating the $C_4$ stream into the light $C_4$ and heavy $C_4$ fractions.

The heavy $C_4$ fraction may be recovered as a bottoms fraction via flow line 16 and fed to isomerization-metathesis reactor 18. When used, ethylene may be co-fed to reactor 18 via flow lines 20 and/or 22. Metathesis reactor 18 may contain one or more beds 24 of a bifunctional isomerization-metathesis according to embodiments disclosed herein, suitable for concurrently isomerizing at least a portion of the 1-butene to 2-butene and converting via metathesis at least a portion of the linear butenes in the heavy $C_4$ fraction, with or without co-fed ethylene, to ethylene and propylene. Hydrogen, when used, may be fed via flow line 23, or may be fed directly to one or more locations along the length of reactor 18.

Effluent from metathesis reactor 18 may be fed via flow line 26 to a separation system 28, which may include, for example, distillation apparatus for separating the effluent into carbon number groups. As illustrated, separation system 28 may fractionate the metathesis product into at least four fractions, including an ethylene-containing fraction recovered vial flow line 30, a propylene-containing fraction recovered via flow line 32, a $C_4$ fraction recovered via flow line 34, and a $C_{5+}$ fraction recovered via flow line 36. The $C_5$ fraction 36 may contain $C_4$ components in addition to $C_5$ and heavier components.

A portion of the $C_2$ fraction recovered via flow line 30 may be purged from the system via flow line 38. The purge from line 38 is utilized primarily to purge trace components that may exist in the ethylene stream, including but not limited to hydrogen, methane, and/or ethane. If desired, at least a portion of the ethylene recovered via flow line 30 may be recycled as ethylene feed via flow line 22 to metathesis reactor 18.

The $C_4$ fraction recovered via flow line 34 may be recycled to metathesis reactor 18 via flow line 40. In some embodiments, at least a portion of the $C_4$ fraction may be recycled to fractionator 12 via flow line 41. In some embodiments, at least a portion of the $C_4$ fraction may be purged, if necessary, via flow line 42. The purge via line 42 may serve to purge $C_4$ paraffins from the system that could otherwise build up to substantial levels as the recycle is increased to allow for high overall conversion of the $C_4$ olefins. Typically, stream 34 may contain between 30 and 60% paraffins as a result of the recycle buildup of paraffins within the system. Although not illustrated, the $C_4$ fraction recovered via flow line 34 may alternatively be fed to a downstream cracking unit, as described in U.S. Provisional Patent Application No. 61/088,221, filed on Aug. 12, 2008, which is hereby incorporated by reference.

As described above, embodiments disclosed herein provide for the concurrent isomerization and metathesis of $C_4$-$C_6$ feeds using a bifunctional catalyst. Bifunctional catalysts according to embodiments disclosed herein may exhibit improved performance in metathesis and isomerization reactions, including extended catalyst cycle times. Use of hydrotalcite support materials may allow bifunctional catalysts disclosed herein to retain a high surface area/gram over a number of catalyst regeneration cycles, allowing for high isomerization and guard bed activity to be maintained. Catalysts according to embodiments disclosed herein may also advantageously allow a greater amount of metathesis catalyst to be loaded per reactor volume as compared to mixed bed catalysts systems, where the additional metathesis catalyst material may allow for extended bed cycle lifespan. Further, a single bifunctional catalyst may eliminate the blending process of two different catalysts of dissimilar morphology during the manufacturing process, decreasing the amount of fines generated during mixing, transport and loading of catalyst in reactor.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of propylene, the process comprising:
   contacting ethylene and a hydrocarbon stream comprising 1-butene and 2-butene with a bifunctional isomerization-metathesis catalyst to concurrently isomerize 1-butene to 2-butene and to form a metathesis product comprising propylene;
   wherein the bifunctional isomerization-metathesis catalyst comprises:
      a catalyst compound comprising at least one element selected from tungsten, tantalum, niobium, molybdenum, nickel, palladium, osmium, iridium, rhodium, vanadium, ruthenium, and rhenium for providing metathesis activity on a support comprising a magnesia-alumina hydrotalcite;
      wherein an exposed surface area of the support provides both
         isomerization activity for the isomerization of 1-butene to 2-butene; and
         reactive sites for the adsorption of catalyst compound poisons.

2. The process of claim 1, wherein the support further comprises an oxide, sulfide, nitride, or hydride of the at least one element from Group IA, IIA, IIB, and IIIA of the Periodic Table of the Elements.

3. The process of claim 1, wherein the support further comprises at least one of magnesium oxide, calcium oxide, barium oxide, lithium oxide, sodium oxide, potassium oxide.

4. The process of claim 1, wherein the catalyst compound further comprises a promoter to reduce acidity.

5. The process of claim 4, wherein the promoter comprises at least one of sodium, potassium, lithium, cesium, and a rare earth element.

6. The process of claim 1, wherein the contacting is conducted in the presence of hydrogen.

7. The process of claim 1, wherein the bifunctional isomerization-metathesis catalyst comprises between 6 and 7 weight percent tungsten oxide.

8. A process for the production of propylene, the process comprising:
   contacting ethylene and a hydrocarbon stream comprising 1-butene and 2-butene with a bifunctional isomerization-metathesis catalyst to concurrently isomerize 1-butene to 2-butene and to form a metathesis product comprising propylene;
   wherein the bifunctional isomerization-metathesis catalyst comprises:
      a catalyst compound comprising at least one element selected from aluminum, gallium, iridium, iron, molybdenum, nickel, niobium, osmium, palladium, phosphorus, rhenium, rhodium, ruthenium, tantalum, titanium, tungsten, and vanadium for providing metathesis activity on a support comprising a magnesia-alumina hydrotalcite co-mingled on a microscopic scale with a catalyst comprising at least one element from Group IA, IIA, IIB, and IIIA of the Periodic Table of the Elements; wherein the co-mingled catalyst particles or an exposed surface area of the support provides both
         isomerization activity for the isomerization of 1-butene to 2-butene; and
         reactive sites for the adsorption of catalyst poisons in the feed.

9. The process of claim 8, wherein the support further comprises an oxide, sulfide, nitride, or hydride of the at least one element from Group IA, IIA, IIB, and IIIA of the Periodic Table of the Elements.

10. The process of claim 8, wherein the support further comprises at least one of magnesium oxide, calcium oxide, barium oxide, lithium oxide, sodium oxide, potassium oxide.

11. The process of claim 8, wherein the catalyst compound further comprises a promoter to reduce acidity.

12. The process of claim 11, wherein the promoter comprises at least one of sodium, potassium, lithium, cesium, and a rare earth element.

13. The process of claim 8, wherein the contacting is conducted in the presence of hydrogen.

14. The process of claim 8, wherein the bifunctional isomerization-metathesis catalyst comprises between 1 and 25 weight percent tungsten oxide.

* * * * *